US006465018B1

(12) United States Patent
Tuttle

(10) Patent No.: US 6,465,018 B1
(45) Date of Patent: *Oct. 15, 2002

(54) DIETARY SUPPLEMENT FOR INCREASING ENERGY, STRENGTH, AND IMMUNE FUNCTION

(76) Inventor: B. David Tuttle, 1830 Stoner Ave., Los Angeles, CA (US) 90025

( * ) Notice: Subject to any disclaimer, the term of this patent is extended or adjusted under 35 U.S.C. 154(b) by 0 days.

This patent is subject to a terminal disclaimer.

(21) Appl. No.: 09/669,977

(22) Filed: Sep. 26, 2000

Related U.S. Application Data

(63) Continuation-in-part of application No. 08/917,022, filed on Aug. 22, 1997, now Pat. No. 6,193,973.

(51) Int. Cl.$^7$ .................... A61K 35/78; C07C 229/00; A23L 1/30
(52) U.S. Cl. .................... 424/728; 424/725; 424/773; 426/648; 426/810; 514/962; 562/563
(58) Field of Search .................... 424/725, 728, 424/773; 562/563; 514/962; 426/648, 810

(56) References Cited

U.S. PATENT DOCUMENTS

| 4,708,949 A | 11/1987 | Liu | 514/26 |
| 5,308,627 A | 5/1994 | Umbdenstock | 424/639 |

OTHER PUBLICATIONS

E. Hultman et al, "Muscle Creatine Loading in Men", Journal of Applied Physiology, vol. 81(1), pp. 232–237 (1996).
Allan Gordon et al, "Creatine Supplementation In Chronic Heart Failure Increases Skeletal Muscle Creatine Phosphate And Muscle Performance", Cardiovascular Research, vol. 30, pp. 413–418 (1995).
Paul L. Greenhaff, "Creatine And Its Application As An Ergogenic Aid", International Journal of Sport Nutrition, vol. 5, pp. S100–S110, (1995).
Ronald J. Maughan, "Creatine Supplementation and Exercise Performance", International Journal of Sport Nutrition, vol. 5, pp. 94–101 (1995).
Tomas C. Welbourne, "Increased Plasma Bicarbonate And Growth Hormone After An Oral Glutamine Load", American Journal of Clinical Nutrition, vol. 61, pp. 1058–1061 (1995).
K.S. Zhao et al, "Enhancement Of The Immune Response In Mice By Astragalus Membranaceus Extracts", Immunopharmacology, vol. 20, pp. 225–234 (1990).
"Creatine: Nature's Muscle Builder", by Ray Sahelian and Dave Tuttle, Avery Publishing Group (Garden City Park, NY) (1997).
"Ginseng: The Energy Herb", by Christopher Hobbs, Botanica Press (Loveland, CO), pp. 24–36, pp. 96–103 (1996).
John Heineman, "Heinerman's Encyclopedia of Healing Herbs & Spices", Prentice Hall (Eaglewood Cliffs), NJ, pp. 38–39 (1996).
Daniel B. Mowrey, Ph.D., "Herbal Tonic Therapies", Keats Publishing, Inc. (New Canaan, CT), pp. 55–59 (1993).
Dave Tuttle, "Glutamine: Athletic Benefits Times Three", Lets Live, Sep., pp. 71–73 (1997).
"Creatin Magnesium Chelate", Think Muscle Newsletter, No. 6, URL: www.thinkmuscle.xom/newsletter/006.htm, pp. 4.

*Primary Examiner*—Christopher R. Tate
(74) *Attorney, Agent, or Firm*—Marvin E. Jacobs

(57) ABSTRACT

A dietary supplement is provided that comprises creatine combined with ginseng and astragalus and, optionally, glutamine. The dietary supplement enhances the general energy boost and muscular strength increase achieved from the consumption of creatine alone, while also increasing immune function.

11 Claims, No Drawings

DIETARY SUPPLEMENT FOR INCREASING ENERGY, STRENGTH, AND IMMUNE FUNCTION

CROSS-REFERENCE TO RELATED APPLICATION

The present application is a continuation-in-part of application Ser. No. 08/917,022, filed Aug. 22, 1997, now U.S. Pat. No. 6,193,973.

TECHNICAL FIELD

The present invention relates generally to dietary supplements, and, more particularly, to a blend of creatine, ginseng, and astragalus, and, optionally, glutamine for increasing energy, strength, and immune function.

BACKGROUND ART

As we age, our bodies undergo a variety of changes. We often lose strength and energy due to declines in hormone levels and a more sedentary lifestyle. These changes can frequently interact with each other to produce compounding effects. For example, the loss in muscle strength increases the likelihood of falls and broken bones, which can lead to further declines in physical activity and strength. While some of these declines in strength and energy levels are inevitable, they can also result from nutritional deficiencies and changes in lifestyle patterns. This is partly responsible for the greater utilization of medical resources by senior citizens and consequent impacts on Medicare expenditures.

One muscle-building substance which does not typically exhibit any significant side effects is creatine, which is derived from reactions involving the amino acids arginine, glycine, and methionine:

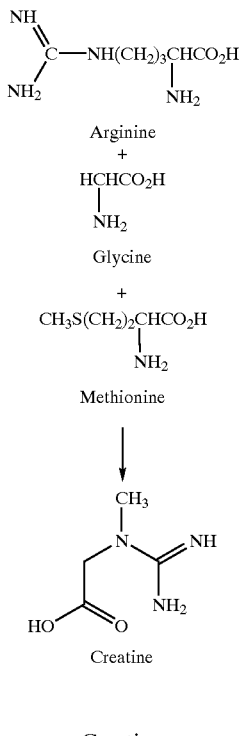

Creatine

Creatine is a nutrient that increases protein synthesis and intra-cellular water levels within the muscle fibers, resulting in greater strength and muscle mass. This boosts daily caloric expenditure, which will lower body-fat stores if food intake is unchanged. A discussion of the benefits may be found in a book by Ray Sahelian and Dave Tuttle, entitled *Creatine: Nature's Muscle Builder*, Avery Publishing Group (1997).

Given the well-established, beneficial effects of creatine for adding strength and power, building lean muscle mass, boosting sports endurance, and helping to reduce body fat, and the rare incidence of associated side effects, it would be desirable to provide creatine in a dietary supplement improved over that already commercially available. Such a dietary supplement should enhance the general energy-boosting and muscular strength-increasing qualities offered by creatine without introducing any harmful side effects. It should be inexpensively manufactured, and comply with all applicable government regulations.

U.S. Pat. No. 5,308,627, entitled "Nutritional Supplement for Optimizing Cellular Health" and issued to A. J. Umbdenstock, Jr., on May 3, 1994, is directed to a nutritional supplement, functioning as a food for special dietary use, to enhance diets and assist persons recovering from addiction to health-damaging substances. The nutritional supplement consists of a mixture of nutrients, specifically, minerals, vitamins, anti-oxidants, amino acids, herbs, and/or other nutrients, which are said to cooperate synergistically in enhancing cellular metabolic pathways and to assist in normalization of cellular function and optimization of cellular health. In one embodiment, the supplement comprises at least one amino acid and at least one herbal antispasmodic substance.

While the '627 patent teaches the use of an "herbal antispasmodic substance" in the treatment of alcoholism (Col. 3, lines 52–65), there is no evidence that ginseng and astragalus (two herbs employed in the present invention), despite centuries of use as individual herbs, have antispasmodic properties. Nor is there any indication that combining aqueous extracts of these herbs with creatine, and, optionally, glutamine, also employed in the practice of the present invention, would produce such antispasmodic properties. Ginseng and astragalus simply are not known to reduce spasms, although they are well-known for many other benefits.

Moreover, Umbdenstock teaches a supplement with at least one enzyme-activating substance and at least one enzyme cofactor. This enzyme-activating substance is a mineral (Col. 6, line 18–19), while the enzyme cofactor is a vitamin (Col. 6, 38–39). There are no vitamins or minerals in the present invention.

Further, while glutamine is included in the dietary supplement taught by the '627 patent (Col. 10, line 12), its function is to permit degradation of harmful $NH_4$ to $NH_3$ for removal in the urine of alcoholics. The present application teaches the use of glutamine to promote the release of growth hormone and to provide a source of energy for the cells of the immune system and the mucosal cells of the intestinal tract in combination with creatine and herbal extracts that are not taught in the '627 patent. Therefore, this patent does not teach art relevant to the present invention.

Further, Umbdenstock proposes the use of an amino acid that "produces an enzyme that acts as a catalyst for the normalized cellular chemical reaction" (Col. 3, lines 54–56). To the best of the present inventor's knowledge, creatine, which is an amino acid, does not produce such an enzyme. Rather, creatine provides an additional substrate for increased resynthesis of ATP by boosting levels of creatine phosphate; see, e.g., *Creatine*, supra, pp. 75–82. While the enzyme creatine kinase does facilitate this reaction, the present inventor does not know of any evidence that supplemental creatine increases levels of creatine kinase, nor is there any reason to suppose that this should occur, inasmuch as creatine kinase is not used up in the reaction.

U.S. Pat. No. 4,708,949, entitled "Therapeutic Composition from Plant Extracts" and issued to Y. Liu on Nov. 24, 1987, discloses a therapeutic composition composed of four plant extracts: ginsenoside, tetramethyl pyrazine, astragalan, and atractylol. These four ingredients are said to be highly effective in treating cerebral vascular disease and the sequelae thereof, whereas the present invention teaches a method for enhancing energy, strength and immune function.

Moreover, the composition taught by the '949 patent is comprised of specific plant chemicals, not extracts of whole herbs. While ginsenoside is contained in ginseng and astragalan is found in astragalus, there are many other active chemicals in each of these herbs. Although ginsenoside content is used as a quality marker in the present invention, it is not the only component with therapeutic properties. In fact, a polysaccharide marker is included in the preferred composition of the present invention so that a range of plant chemicals will be included instead of simply ginsenoside. Tetramethyl pyrazine and atractylol, the other two extracts in the '949 patent, are not found in the present invention. Therefore, this patent does not teach art relevant to the present invention.

Further, Liu's extraction process involves ethanol. The preferred composition of the present invention utilizes only aqueous extraction to ensure that older individuals with possibly compromised immune systems do not consume a dietary supplement with solvent residues.

Thus, a need remains for a creatine-based supplement for increasing energy, strength, and immune function.

DISCLOSURE OF INVENTION

In accordance with the present invention, a dietary supplement is provided that comprises creatine combined with ginseng and astragalus and, optionally, glutamine. The present supplement therefore enhances the general energy boost and muscular strength increase achieved from the consumption of creatine alone, while also increasing immune function. The components are provided together in at least one capsule.

More particularly, the dietary supplement of the present invention will help mature individuals overcome the problems noted above by providing the specified nutrients that work together to boost energy and enhance muscle growth. The dietary supplement will also increase the strength and sense of vitality of such mature individuals.

BEST MODES FOR CARRYING OUT THE INVENTION

Reference is now made in detail to a specific embodiment of the present invention, which illustrates the best mode presently contemplated by the inventor for practicing the invention. Alternative embodiments are also briefly described as applicable.

The dietary supplement of the invention comprises creatine, ginseng, and astragalus, optionally combined with glutamine. The dietary supplement composition is preferably put into a capsule using known technology. The total daily dosage for an adult is 3 to 6 capsules per day. The capsules are preferably consumed with two or three meals to provide a relatively even intake of the nutrients in the composition throughout the day. However, the dosage regimen is flexible as long as the total daily dosage is achieved.

The creatine employed in the practice of the present invention is of a pharmaceutical grade that is commercially available from various manufacturing sources. It is preferably in the form of creatine monohydrate. However, other creatine derivatives, such as creatine citrate and creatine pyruvate, may also be employed in the practice of the invention.

In addition to creatine, the present dietary supplement contains two other complementary herbal extracts, ginseng and astragalus, and, optionally, an amino acid, glutamine, to provide benefits that enhance the nutritional quality of creatine alone. Thus, there are two possible combinations:

creatine, ginseng, and astragalus, and creatine, ginseng, astragalus, and glutamine.

Each capsule of the invention preferably contains the following ingredients, within the following ranges: (a) about 250 to 1500 mg of creatine monohydrate; (b) about 100 to 600 mg of ginseng (c) about 100 to 600 mg of astragalus; and, if employed, (d) about 100 to 600 mg of L-glutamine.

Creatine

Creatine is a naturally occurring nutrient. It is found in the skeletal and cardiac muscles of all animals, including man. While it would be theoretically possible to get enough creatine to increase strength levels from eating large quantities of meat, the cholesterol and fat content of these foods makes this highly inappropriate. The preferred alternative is to use creatine monohydrate, a manufactured nutrient that is both inexpensive and highly effective. Alternatively, the creatine may be in the form of creatine citrate and/or creatine pyruvate and/or creatine chelates, such as creatine magnesium chelate, alone or in combination with creatine monohydrate.

More than 50 studies have analyzed the effects of creatine monohydrate during the 1990s. These studies have found that creatine increases muscular strength, peak torque production and mean power output. It does this by providing more raw material for the resynthesis of ATP, or adenosine triphosphate. This allows the muscles to remain within the ATP-CP energy pathway longer, and lengthens the time before muscular contraction ceases due to lactic-acid buildup. There is also an increase in lean muscle mass and protein synthesis due to a creatine-induced rise in intracellular (but not subcutaneous) water levels. While these changes are maximized with exercise, they also occur in sedentary individuals. A 1996 study by Hultman with individuals told to avoid physical exercise found that a daily dosage of 3 grams raised intracellular creatine concentrations to effective levels; see, e.g., E. Hultman et al, "Muscle creatine loading in men", *Journal of Applied Physiology*, Vol. 81(1), pp. 232–237 (1996).

The transport mechanism used to shuttle creatine into the muscle cells involves insulin. The required spike in insulin levels is produced by the carbohydrates in a regular meal (40 to 50 grams), hence the recommendation that the dietary supplement be taken with meals. Due to its ability to increase lean mass, creatine also boosts the body's daily caloric expenditure. (Each pound of muscle requires approximately 20 calories per day to "live"). If use of the dietary supplement of the invention increases lean mass by 5 pounds, this boost in caloric requirements would result in a loss of a pound of body fat per month if food intake is unchanged.

Preferably, creatine monohydrate that has been manufactured in accordance with the teachings of U.S. Pat. No. 5,719,319 is employed in the practice of the present invention. Alternatively, other technology that produces equivalent or lower impurity levels may be employed.

Ginseng

Preferably, *Panax ginseng* is employed as the preponderant herb. However, other forms of ginseng may alternatively be used. Such other forms include, but are not limited to, *Panax quinquefolius, Panax notoginseng, Eleutherococcus senticosus*, and *Acanthopanax senticosus*. The ginseng used in the formulation of the invention should be a lyophilized or air-dried aqueous extract obtained from roots with a total saponin content of not less than 4.0 percent.

Ginseng has been revered in China as the King of Herbs for centuries. It helps to replenish the qi, or life force, of the body through a number of mechanisms. Ginseng is an adaptogen, which means that it works with the body to help restore balance. Chinese practitioners use it as a tonic to increase physical strength and energy and promote the proper functioning of the body's organs. They also use it to treat fatigue. Ginseng builds stamina and endurance by enhancing the body's ability to adapt to stress. It was used extensively in former Soviet countries as a way to boost strength and athletic performance.

The dietary supplement of the present invention preferably contains primarily Chinese or Korean ginseng, which is recommended for its warmer qualities. *Panax ginseng* has additional properties that will be of interest to mature individuals. It strengthens the heart muscle and stimulates the immune system. It also increases cerebral circulation, which enhances memory, alertness and other cognitive functions. Some of the active principles in the herb, known as ginsenosides, have antioxidant properties as well. These benefits have been verified in over 3,000 studies conducted in the last 50 years.

The preferred composition contains lesser amounts of *Panax quinquefolius*, also known as American ginseng. This herb has stress-reducing qualities that help to balance the warmer properties of *Panax ginseng*. It also promotes proper functioning of the immune system.

Preferably, lyophilized or air-dried aqueous extracts of Panax ginseng root and *Panax quinquefolius* root are employed in the practice of the present invention in a ratio of 60% *Panax ginseng* and 40% *Panax quinquefolius*. Both herbal extracts preferably have a ginsenoside content of not less than 10% as measured by ultraviolet visible light spectrophotometry absorbance (UV) and a polysaccharide content of not less than 10% as measured by UV. Further, the extracts preferably have levels of quintozene and other pesticides and heavy metals that are below U.S. Environmental Protection Agency detection levels.

Astragalus

Astragalus is employed in the form of *Astragalus membranaceous* and should be the lyophilized or air-dried aqueous extract of the root of the plant. Astragalus works with ginseng to build energy levels, heighten immune-system activity, and increase the body's ability to adapt to stress.

While largely unknown in Western countries, astragalus has been used for thousands of years in traditional Chinese medicine as part of the Fu-Zheng therapy to enhance natural defense mechanisms. It is sometimes combined with ginseng in tonics because of its interactive actions with that herb. Astragalus is particularly effective in the sphere of influence of the spleen. The Chinese consider the spleen to be the middle burner, where the body's energy builds.

Astragalus is able to supplement this energy when it is deficient, making it an excellent long-term energy builder. It has been used by Chinese herbalists to treat every type of fatigue and exhaustion.

The herb is also said to stabilize the exterior of the body and increase its resistance to disease by increasing the circulation of wei qi, or protective life force, on the body's surface. This enhances immune function and boosts the body's ability to adapt to stress. Astragalus stimulates the proliferation of stem cells, macrophages and lymphocytes as well, helping the immune system to hold off invading organisms. It has even been shown to increase the life span of human cells in culture.

Preferably, lyophilized or air-dried aqueous extracts of *Astragalus membranaceous* with a total flavonoid content of not less than 1% as measured by UV and a polysaccharide content of not less than 20% as measured by UV are employed in the practice of the present invention. Further, the extracts preferably have levels of pesticides and heavy metals that are below U.S. Environmental Protection Agency detection levels.

Glutamine

Glutamine is an amino acid that promotes the release of growth hormone, which also increases strength and lean muscle mass. Glutamine also promotes better assimilation of nutrients and speeds up recuperation. Preferably, the levo form, L-glutamine, is employed in the practice of the invention.

Glutamine is an important amino acid for mature individuals. It boosts the secretion of growth hormone from the pituitary gland, which can help offset the reductions in this vital hormone that occur with aging. Growth hormone has a major role in the growth and retention of muscle due to its ability to promote cell division and proliferation in the body. It increases the amount of amino acids transported across the cell membrane, which provides the raw material needed for more protein synthesis. This gives the formula another mechanism to increase strength and muscle mass. Growth hormone even boosts the level of free fatty acids in the blood, resulting in greater use of fats as an energy source and the sparing of available proteins and carbohydrates. By raising the body's energy expenditure at rest, it works beneficially with creatine to help reduce body-fat levels.

Glutamine plays a vital role in the immune system. Many of the cells of this system use glutamine for fuel. Studies have shown that supplemental glutamine speeds recuperation and helps people regain the strength they lose after an illness. Glutamine also provides fuel for the mucosal cells of the intestines, which can improve the assimilation of nutrients. It regulates the body's acid-base balance as well. This neutralizes the high levels of lactic acid that build up during exercise.

Dietary Supplement of the Present Invention

In a preferred composition of the dietary supplement of the present invention, the ratio of creatine monohydrate relative to the other three ingredients is approximately 3:1:1:1, and is represented by the following formulation, in which the capsule or capsules contain about:

| | |
|---|---|
| creatine monohydrate | 1,000 mg |
| ginseng (*Panax ginseng* and *Panax quinquefolius*) | 350 mg |
| astragalus (*Astragalus membranaceous*) | 350 mg |
| L-glutamine | 350 mg. |

A suggested dosage is one or two capsules with breakfast, lunch and dinner, or a total of three to six capsules per day.

A more preferred composition is based on the following ratios to realize full maximum effectiveness of the formulation:

| | |
|---|---|
| Creatine to total herbal extract: | 2:1 |
| Total ginseng to *Astragalus membranaceous* | 1:1 |
| *Panax ginseng* to *Panax quinquefolius* | 3:2. |

The foregoing ratios result in the following ratios for the herbal extract:

| | |
|---|---|
| *Panax ginseng* | 30% |
| *Panax quinquefolius* | 20% |
| *Astragalus membranaceous* | 50%. |

A maximum variation of plus or minus 10% in the foregoing ratios is permitted for the more preferred composition. Three examples of acceptable combinations are as follows:

| | | | |
|---|---|---|---|
| Creatine monohydrate | 500 mg | 600 mg | 750 mg |
| *Panax ginseng* | 75 mg | 90 mg | 100 mg |
| *Panax quinquefolius* | 50 mg | 60 mg | 80 mg |
| *Astragalus membranaceous* | 125 mg | 150 mg | 200 mg |

In the more preferred composition of the present invention, the three herbs are mixed in the specified ratios prior to initiation of the extraction process. This maximizes the interactive properties of the finished extract.

No adverse side effects are reported in the literature at the dosages indicated herein for the listed components.

Older individuals with decreased muscle mass and energy levels will benefit from the dietary supplement of the present invention. Since creatine and L-glutamine boost strength and protein synthesis, they both help to reduce the muscle wasting process that can occur with disease and the aging process. The interactive effects of ginseng and astragalus will enhance immune function, while the interactive effects of creatine, ginseng and astragalus will help to maintain and increase energy levels in these individuals. Being more muscular and energetic can also lead to an improved sense of well-being, resulting in older individuals who look and feel years younger. Stronger muscles will lead to fewer falls and bone fractures, too. Finally, use of the dietary supplement by older individuals may motivate users to continue exercising, which itself is known to lead to stronger bones and a healthier heart.

EXAMPLES

The dietary supplement of the present invention increases strength, energy and immune function in baby boomers and older individuals. To confirm these benefits, a 12-week study is conducted using a placebo-controlled methodology. Fifty test subjects age 45 to 70 are divided into two groups of equal size and randomized in a double-blind protocol. All test subjects are physically active male or female volunteers who-are healthy, not obese and not taking medications on a regular basis. During the 12-week period, test subjects are instructed to maintain their current activity patterns. They are also told to not change their diet in any way, including total caloric intake, macronutrient composition and micronutrient consumption.

Both groups are instructed to take two capsules with breakfast, lunch and dinner. Each capsule given to the experimental group contains the following: 750 mg of creatine monohydrate, 100 mg of *Panax ginseng*, 80 mg of *Panax quinquefolius*, and 200 mg of *Astragalus membranaceous*. Each capsule given to the control group contains 1,100 mg of a maltodextrin placebo. All capsules are of the same shape, color and size to ensure that the test subjects and researchers are not aware who is in the experimental and control groups.

All test subjects are measured at three times: pre-test, Week 6 and Week 12 (post-test). There are a total of seven variables: eccentric power, concentric power, eccentric total work effort, concentric total work effort, vigor, fatigue, and CD4/CD8 ratio.

Strength

The word "strength" has a number of connotations in everyday usage. Technically, strength is the maximal force that a muscle or muscle group can generate. This is referred to as the one-repetition maximum, or 1-RM. However, given the ages of the test subjects, it is considered inappropriate to ask them to perform such a potentially dangerous test. Therefore, power and total work effort are measured instead.

Power is the functional application of both strength and speed, and is what many people think of as strength. All subjects perform a maximal power output isokinetic test at $60°$ $sec^{-1}$ for the knee extensors using both legs. Both eccentric and concentric contractions are measured. The greatest power output occurs during eccentric (lengthening) contractions, while concentric (shortening) contractions permit the greatest total work effort. This power output measurement is calculated in kilograms (kg). The following results are anticipated:

| | Eccentric Power (mean) | % Increase from Pre-test | Concentric Power (mean) | Increase from Pre-test |
|---|---|---|---|---|
| Pre-test | 37 kg | — | 30 kg | — |
| 6 weeks | 40 kg | 9% | 32 kg | 7% |
| 12 weeks | 42 kg | 14% | 33 kg | 10% |

After a 15-minute rest period, test subjects also perform a bilateral isotonic muscular fatigue test of the knee extensors to exhaustion to calculate total work effort. Eccentric and concentric work efforts are measured in joules 0). The anticipated results are:

| | Eccentric Total Work Effort (mean) | % Increase From Pre-test | Concentric Total Work Effort (mean) | % Increase From Pre-test |
|---|---|---|---|---|
| Pre-test | 580 j | — | 1,125 j | — |
| 6 weeks | 670 j | 15% | 1,350 j | 20% |
| 12 weeks | 700 j | 22% | 1,460 j | 30% |

Energy

Enhanced energy levels are perceived as an increase in vigor and/or a reduction in fatigue. The Profile of Mood States (POMS) is a widely used measure of changes in mood states. It consists of 65 words or brief phrases and contains six subscales: tension, depression, anger, vigor, fatigue and confusion.

All study participants are tested for the POMS vigor and fatigue subscales. They are asked to carefully read each item and then respond to a 5-point Likert scale ranging from 1

(not at all) to 5 (extremely) based on how they are feeling the week and day that they complete the inventory. An increase in vigor and a reduction in fatigue is anticipated:

|  | Vigor Subscale | % Change From Pre-test | Fatigue Subscale | % Change From Pre-test |
|---|---|---|---|---|
| Pre-test | 18.0 | — | 7.5 | — |
| 6 weeks | 19.4 | +8% | 6.0 | −20% |
| 12 weeks | 20.5 | +14% | 5.0 | −33% |

Immune Function

There are two types of immunity: specific (adaptive) and nonspecific (innate). Specific immunity has the characteristics of adaptability, memory and learning, and is carried out by antibodies and other specialized cells. The lymphocyte is the cellular component of the specific immune system. These lymphocytes are divided into two subsets: T-cells and B-cells. T-cells recognize and selectively kill virus-infected cells, fungi and some other foreign cells. All mature T-cells become either CD4 (T-helper cells) or CD8 (T-suppressor cells). The ratio between these two cell types is a frequently used indicator for the health of the specific immune system.

All test subjects are measured for CD4/CD8 ratio. Blood samples are taken from the forearms of the test subjects at least 15 minutes prior to the strength tests noted earlier. The CD4/CD8 ratio is measured using flow cytometry. The anticipated results are:

|  | CD4/CD8 ratio (mean) | % Increase From Pre-test |
|---|---|---|
| Pre-test | 2.50 | — |
| 6 weeks | 2.75 | 10% |
| 12 weeks | 2.90 | 16% |

Thus, there has been disclosed a dietary supplement comprising creatine, ginseng, and astragalus, and, optionally, glutamine. It will be readily apparent to those skilled in the art that various changes and modifications of an obvious nature may be made, and all such changes and modifications may be made without departing from the spirit of the invention, as defined by the appended claims.

What is claimed is:

1. A dietary supplement consisting essentially of the following formulation together in at least one capsule:
   (a) about 250 to 1500 mg of creatine or a compound thereof selected from the group consisting of creatine monohydrate, creatine citrate, creatine pyruvate, and creatine magnesium chelate;
   (b) about 100 to 600 mg of ginseng extract obtained from the roots *Panax ginseng* and *Panax quinquefolius* having a total saponin content of at least 4.0%; and
   (c) about 100 to 600 mg Astragalus extract.

2. The dietary supplement of claim 1, wherein said creatine compound is creatine monohydrate.

3. The dietary supplement of claim 1, wherein the Astragalus extract *Astragalus membraneous* extract.

4. The dietary supplement of claim 3, wherein the following ratios are employed:

| Creatine to total herbal extract: | 2:1 |
|---|---|
| Total Ginseng extract to *Astragalus membraneous* extract | 1:1 |
| *Panax ginseng* extract to *Panax quinquefolius* extract | 3:2. |

5. The dietary supplement of claim 3, wherein the following percentages of said extracts are employed:

| *Panax ginseng* extract | 30% |
|---|---|
| *Panax quinquefolius* extract | 20% |
| *Astragalus membraneous* extract | 50%. |

6. The dietary supplement of claim 1, comprising a composition selected from the group consisting of about:
   (a) 500 mg creatine monohydrate, 75 mg Panax ginseng extract, 50 mg *Panax quinquefolius* extract, and 125 mg *Astragalus membraneous* extract;
   (b) 600 mg creatine monohydrate, 90 mg *Panax ginseng* extract, 60 mg *Panax quinquefolius* extract, and 150 mg *Astragalus membraneous* extract; and
   (c) 750 mg creatine monohydrate, 100 mg *Panax ginseng* extract, 80 mg *Panax quinquefolius* extract, and 200 mg *Astragalus membraneous* extract.

7. A dietary supplement consisting essentially of the following formulation together in at least one capsule:
   (a) about 250 to 1500 mg of creatine or a compound thereof selected from the group consisting of creatine monohydrate, creatine citrate, creatine pyruvate, and creatine magnesium chelate;
   (b) about 100 to 600 mg of ginseng extract obtained from the roots *Panax ginseng* and *Panax quinquefolius* having a total saponin content of at least 4.0%;
   (c) about 100 to 600 mg Astragalus extract; and
   (d) about 100 to 600 mg of L-glutamine.

8. The dietary supplement of claim 7, consisting essentially of the following formulation together in said at least one capsule:

| creatine monohydrate: | 1,000 mg |
|---|---|
| Ginseng extract | 350 mg |
| Astragalus extract | 350 mg |
| L-glutamine | 350 mg. |

9. A method of increasing energy and muscular strength of an individual comprising having the individual ingest the dietary supplement of any one of claims 1–8 while participating in an exercise program.

10. The method according to claim 9, whereby the Ginseng extract consist of a major amount of *Panax ginseng* extract and a minor amount of *Panax quinquefolius* extract.

11. The method according to claim 9, wherein the creatine compound is creatine monohydrate.

* * * * *